United States Patent [19]

Finizio

[11] Patent Number: 4,548,943

[45] Date of Patent: Oct. 22, 1985

[54] ANTIINFLAMMATORY, ANALGESIC, OR ANTI-PRIMARY DYSMENORRHEAL ARYLMETHYLENE- AND ARYLMETHYLINDENOIMIDAZOLES

[75] Inventor: Michael Finizio, Wilmington, Del.

[73] Assignee: E. I. Du Pont de Nemours and Company, Wilmington, Del.

[21] Appl. No.: 609,313

[22] Filed: May 11, 1984

[51] Int. Cl.[4] .................. A61K 31/415; C07D 235/02; C07D 401/06

[52] U.S. Cl. .................... 514/393; 546/271; 548/323; 548/108; 514/338

[58] Field of Search .............. 548/323, 302, 108; 546/271; 424/273 R, 263; 514/338, 393

[56] References Cited

U.S. PATENT DOCUMENTS 3,792,057  2/1974  Jensen et al. .......... 548/323
3,856,818  12/1974 Hauck et al. .......... 548/323

FOREIGN PATENT DOCUMENTS 0061712  10/1982  European Pat. Off. ......... 548/323

OTHER PUBLICATIONS

Stedman's Medical Dictionary, 23rd. Ed., Williams & Wilkins Co., Balt., 1976, p. 432

Primary Examiner—Richard A. Schwartz
Assistant Examiner—Kurt G. Briscoe

[57] ABSTRACT

Antiinflammatory, analgesic and prostaglandin synthetase inhibitory arylmethylene- and arylmethylindenoimidazoles useful for the treatment of pain, inflammation, and primary dysmenorrhea having the structure

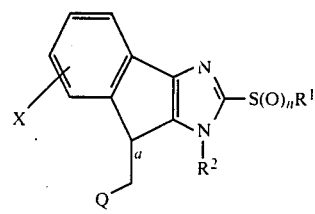
(Ia)

or

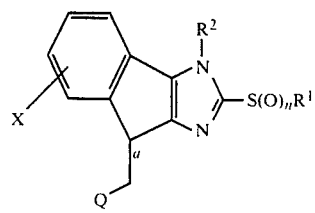
(Ib)

19 Claims, No Drawings

ANTIINFLAMMATORY, ANALGESIC, OR ANTI-PRIMARY DYSMENORRHEAL ARYLMETHYLENE- AND ARYLMETHYLINDENOIMIDAZOLES

BACKGROUND OF THE INVENTION

European patent application No. 0,061,712, published Oct. 6, 1982 discloses compounds of the formula,

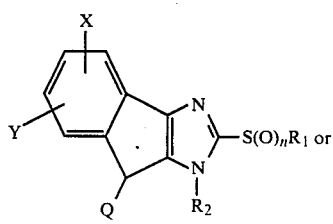

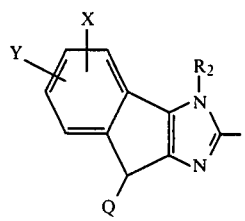

where Q is pyridyl, thienyl or a group of the formula

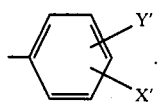

These compounds are disclosed as possessing antiinflammatory and/or analgesic activity, U.S. Pat. No. 3,792,057 issued to Jensen on Feb. 12, 1974, discloses compounds of the formula

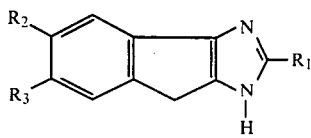

where $R_1$ may be methylthio as inhibitors of phenylethanolamine-N-methyl transferase and also as fungicides and coccidiostats.

There is a continuing need for safe and effective antiinflammatory agents. Inflammation is a disease process characterized by redness, fever, swelling and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited, however, because of toxicity and adverse side-effects. Many produce gastric irritation and other effects, such as changes in blood cells and in the central nervous system. Adrenocortical steroids produce gastric irritation and suppression of normal adrenal function.

Dysmenorrhea is a painful condition associated with menstruation which affects an estimated 30–50 percent of women of childbearing age causing the loss of more than 140 million working hours per year [J. L. Marx, Science, 205, 175 (1979)]. The symptoms of dysmenorrhea include nausea, vomiting, diarrhea, and headache. Abnormally high levels of prostaglandin compounds occur in the endometrium and menstrual fluid of patients suffering from primary dysmenorrhea. Prostaglandins are known to cause uterine contractions, sensitize nerve endings to pain, and cause the typical symptoms of the condition. Treatment of dysmenorrhea with prostaglandin synthetase inhibitors reduces prostaglandin levels and relieves the symptoms of dysmenorrhea [M. R. Henzl and A. Izu, Acta. Obstet. Gynecol. Scand. Suppl., 87, 105 (1979) and W. Y. Chan, M. Y. Dawood, and F. Fuchs, Am. J. Obstet. Gynecol., 135, 102 (1979)].

There is thus a clear need for improved antiinflammatory agents, especially ones which also possess activity as prostaglandin synthetase inhibitors which would be independently useful for treatment of primary dysmenorrhea.

The present invention results from efforts to develop new anti-arthritic compounds with good antiinflammatory activity and minimal side effects that could be more effective in treating arthritis than presently available drugs.

In addition to antiinflammatory properties, some compounds of this invention demonstrate analgesic activity in a test procedure. This additional property is desirable in treatment of arthritis or related diseases; however, such compounds can be employed solely to alleviate pain.

In addition, compounds of this invention are inhibitors of prostaglandin synthetase and as such are useful for the treatment of primary dysmenorrhea.

SUMMARY OF THE INVENTION

According to the invention, there is provided a compound of the formula:

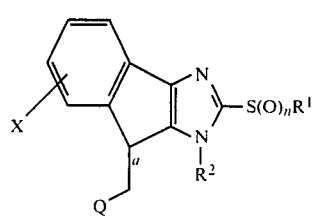
(Ia)

or

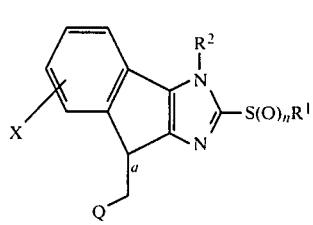
(Ib)

where
n is 0, 1 or 2,
$R^1$ is $C_1$–$C_2$ alkyl, $CF_3$ or $CF_2CHF_2$;
$R^2$ is H, $C_1$–$C_2$ alkyl, $CH(R^3)OR^4$, 2-tetrahydrofuranyl, 2-tetrahydropyranyl, $COOR^4$ or $COR^5$;
where
$R^3$ is H or $CH_3$;
$R^4$ is $CH_3$, $C_2H_5$ or

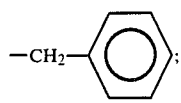

and

R$^5$ is CH$_3$, or C$_2$H$_5$; with the proviso that when R$^2$ is COOR$^4$ or COR$^5$, then n is 0;

a is a single bond or a double bond having either the E or Z configuration with the proviso that when the double bond is Z, then n is 1 or 2;

Q is pyridyl, thienyl or

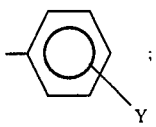

and

X and Y are independently H, F, Cl, Br, NO$_2$, OCH$_3$, OC$_2$H$_5$, N(C$_1$-C$_2$ alkyl)$_2$, CH$_3$, C$_2$H$_5$ or S(O)$_m$ C$_1$-C$_2$ alkyl where m is 0, 1 or 2; or a pharmaceutically acceptable acid salt thereof when n is 0 or metal salts thereof when n is 2 and R$^2$ is H.

Preferred compounds are those compounds of the above formula where a is a double bond.

More preferred compounds are those where:
n is 0 or 2;
R$^1$ is CF$_3$ or CF$_2$CHF$_2$;
R$^2$ is H;
a is a double bond;
Q is

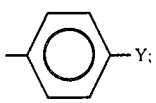

and

X and Y are independently H, F, Cl, OCH$_3$, CH$_3$ or S(O)$_m$CH$_3$ where m is 0 or 2.

Most preferred compounds are those immediately above where R$^1$ is CF$_3$.

Specifically preferred are:

1,8-Dihydro(or 3,8-dihydro)-2-(trifluoromethylsulfonyl)-8-(phenylmethylene)indeno[1,2-d]imidazole, E isomer.

1,8-Dihydro(or 3,8-dihydro)-2-(trifluoromethylsulfonyl)-8-[(4-methoxyphenyl)methylene]indeno[1,2-d]imidazole, E isomer.

1,8-Dihydro(or 3,8-dihydro)-2-(trifluoromethylsulfinyl)-8-[(4-fluorophenyl)methylene]indeno[1,2-d]imidazole, E isomer.

Also provided are pharmaceutical compositions containing at least one of the aforesaid compounds and methods of using them to treat inflammation and/or alleviate pain in mammals.

Additionally provided are novel intermediates of the formula:

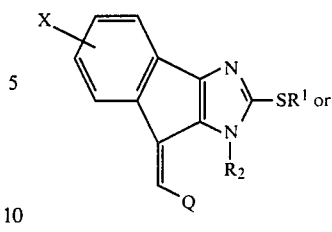

(Ic)

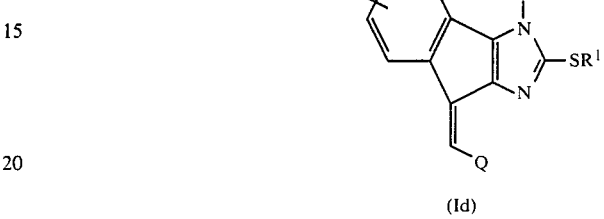

(Id)

where
R$^1$ is C$_1$-C$_2$ alkyl, CF$_3$ or CF$_2$CHF$_2$;
R$^2$ is H, C$_1$-C$_2$ alkyl, CH(R$^3$)OR$^4$, 2-tetrahydrofuranyl, 2-tetrahydropyranyl, COOR$^4$ or COR$^5$;
where
R$^3$ is H or CH$_3$;
R$^4$ is CH$_3$, C$_2$H$_5$ or

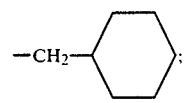

and
R$^5$ is CH$_3$ or C$_2$H$_5$;
Q is pyridyl, thienyl or

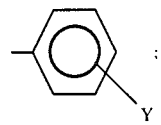

and
X and Y are independently H, F, Cl, Br, NO$_2$, OCH$_3$, OC$_2$H$_5$, N(C$_1$-C$_2$ alkyl)$_2$, CH$_3$, C$_2$H$_5$ or S(O)$_m$-C$_1$-C$_2$ alkyl where m is 0, 1 or 2.

DETAILED DESCRIPTION

Synthesis

The compounds of this invention can be prepared from properly substituted 1,8-dihydro-2-(substituted thio)indeno[1,2-d]imidazoles IIa or 3,8-dihydro-2-(substituted thio)indeno[1,2-d]imidazoles IIb or mixtures of IIa and IIb where R$^2$ is a base-stable, acid-labile substituent such as 1-ethoxyethyl, 2-tetrahydropyranyl, or 2-tetrahydrofuryl. These can be prepared from the corresponding compounds IIIa/IIIb by reaction with a suitable reagent such as 2,3-dihydropyran or ethyl vinyl ether, in the presence of a suitable acid such as dichloroacetic acid, optionally followed by chromatographic separation of the two isomers. Alternatively, when R$_2$ is C$_1$-C$_2$ alkyl, the compounds IIa/IIb are prepared by reaction of IIIa/IIIb with methyl or ethyl iodide in the presence of a base.

Compounds IIIa/IIIb can be prepared from the corresponding 1,8-dihydro(or 3,8-dihydro)-indeno[1,2-d]imidazole-2-thiols IVa/IVb by alkylating the thiols with a suitable alkylating agent such as methyl iodide. Compounds IIIa/IIIb where $R^1$ is trifluoromethyl can be prepared by irradiating a mixture of the thiol (IVa/IVb) and trifluoromethyl iodide as alkylating agent in liquid ammonia. An inert solvent such as ether, tetrahydrofuran or the like is usually added to provide a homogeneous solution. Compounds where $R^1$ is 1,1,2,2-tetrafluoroethyl can be prepared by reacting the thiols (IVa/IVb) with tetrafluoroethylene. Similar addition reactions of tetrafluoroethylene are described in D. C. England et al., *J. Am. Chem. Soc.*, 82, 5116 (1960) and K. E. Rapp et al., *J. Am. Chem. Soc.*, 72, 3642 (1950). For the purpose of this disclosure tetrafluoroethylene is considered an alkylating agent.

The synthesis of compounds IVa/IVb involves conversion of the properly substituted ketones to the corresponding tosyloximes; these in turn are subjected to Neber rearrangement [P. W. Neber and A. Friedolsheim, Ann., 499, 109 (1926)] to produce 2-amino-1-indanone hydrochlorides which, upon treatment with potassium thiocyanate, give 1,8-dihydro(or 3,8-dihydro)indeno[1,2-d]imidazole-2-thiols, as shown in Scheme I. (This sequence is similar to the one reported by D. Huckle, I. M. Lackhart and M. Wright, J. Med. Chem., 12(3), 277-79 (1969) for the preparation of 3-amino-4-chromanones.)

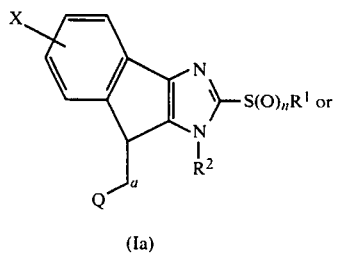

(Ia)

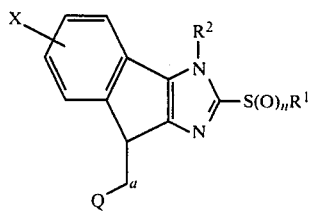

(Ib)

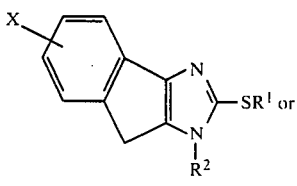

(IIa)

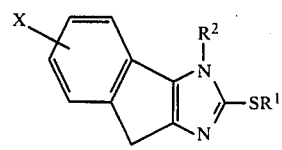

(IIb)

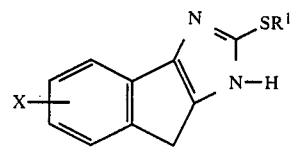

(IIIa)

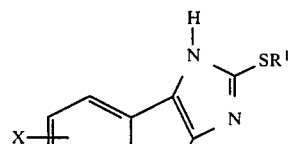

(IIIb)

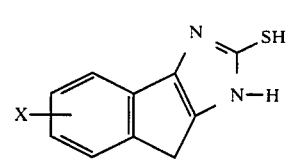

(IVa)

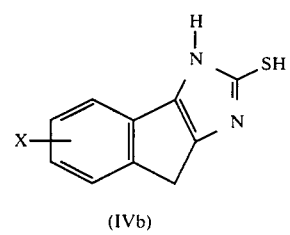

(IVb)

Scheme 1

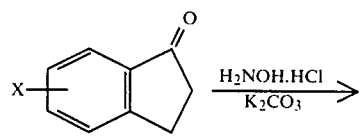

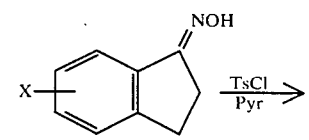

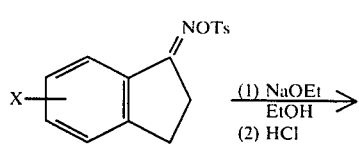

-continued

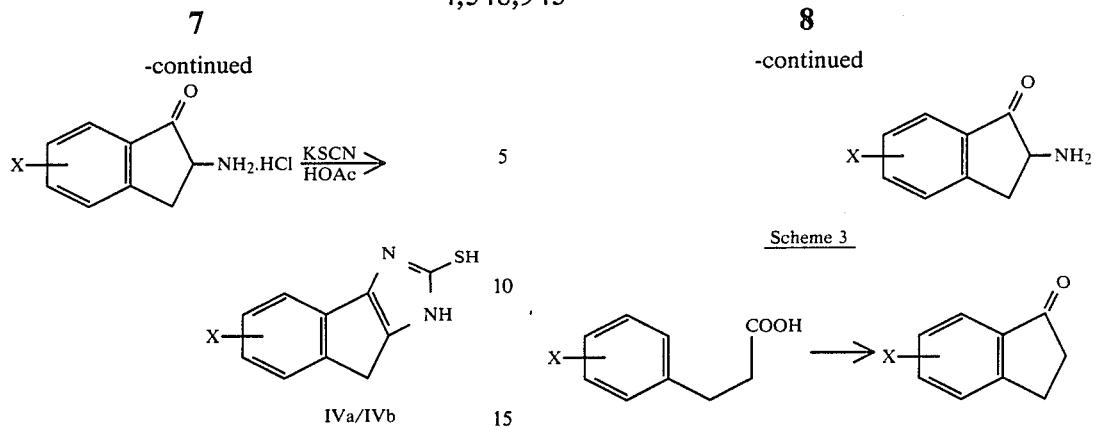

IVa/IVb

The 2-amino-1-indanones of Scheme I can also be prepared by conversion of the appropriate ketones into isonitroso ketones (Org. Syn., II, 363) and catalytic reduction of the latter [S. Kimoto et al., *Yakusaku Zasshi*, 88(10), 1323–8, (1968)] as illustrated in Scheme 2. This sequence is the one reported by H. Paul and K. Walter, *J. Prakt. Chem.*, 28, 297–304 (1965), and by N. P. Jensen et al., U.S. Pat. No. 3,792,057 (Feb. 12, 1974) to prepare compounds having structures IVa/IVb.

Some of the starting ketones are commercially available; these and others can be prepared by cyclization of the corresponding dihydrocinnamic acids with a strong acid such as aluminum chloride, sulfuric acid, polyphosphoric acid, or hydrofluoric acid. (Scheme 3).

Compounds Ia/Ib where a is a double bond and n=0 can be prepared from IIa or IIb or a mixture of IIa and IIb by condensation with an appropriately substituted aromatic aldehyde in the presence of a basic catalyst such as sodium ethoxide, in an appropriate solvent such as ethanol. The reaction mixture can then be optionally treated with a dilute aqueous solution of an acid such as hydrochloric acid to remove the acid-labile substituent on the imidazole nitrogen. In those cases where a mixture of geometric isomers about the double bond are obtained, the isomers can be separated by chromatography on silica gel.

The 1,8-dihydro(or 3,8-dihydro)-8-arylmethyleneindeno[1,2-d]-imidazole-2-sulfides can then be oxidized to the corresponding sulfoxides or sulfones by using oxidizing agents such as m-chloroperbenzoic acid [P. C. Tweit et al., J. Med. Chem., 16, 1161 (1973)] or sodium metaperiodate [N. J. Leonard and C. R. Johnson, *J. Org. Chem.*, 27, 282 (1962)].

Scheme 2

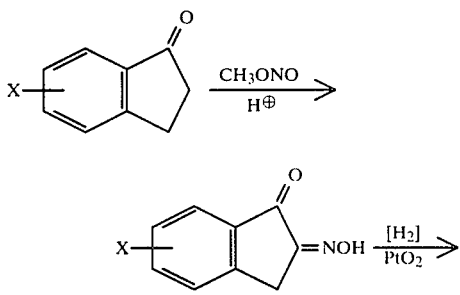

-continued

Scheme 3

Compounds Ia/Ib where a is a single bond can be prepared from the corresponding Z or E olefins by reduction using a suitable reducing agent, such as hydrogen in the presence of a suitable catalyst such as palladium, in a suitable solvent such as acetic acid.

Compounds Ia/Ib where $R^2$ is methyl, ethyl, $COOR^4$, or $COR^5$ can be prepared by alkylation or acylation of the corresponding compounds with $R^2=H$. These reactions can be conducted in the presence or absence of a base, such as potassium carbonate, pyridine, triethylamine, potassium t-butoxide, or sodium hydride. Examples of alkylating and acylating agents capable of introducing $R^2$ groups are methyl iodide, acetic anhydride, acetyl chloride, ethyl chloroformate and benzoyl chloride. Compounds where $R^2$ is 2-tetrahydrofuryl, 2-tetrahydropyranyl, or $CH(R^3)OR^4$ can be prepared from the corresponding compounds where $R^2=H$ by treatment with an appropriate reagent such as ethyl vinyl ether or 2,3-dihydropyran in the presence of an acid such as dichloroacetic acid.

In the following examples, temperatures are in degrees centigrade.

PREPARATION OF INTERMEDIATES 2,3-DIHYDRO-1-(HYDROXYIMINO)-1H-INDENE

A mixture of 1-indanone (100 g), hydroxylamine HCl (183 g), potassium carbonate (183 g), methanol (1700 ml) and water (170 ml) was heated at reflux for 18 hours, then cooled and poured into water. The title compound was filtered, washed with water and air-dried.

Yield: 100.8 g; m.p. 141.5°–143.7°.

2,3-DIHYDRO-1-[(4-METHYLPHENYL)SULFONYLOXIMINO]-1H-INDENE

A solution of p-toluenesulfonyl chloride (266 g) in pyridine (300 ml) was added dropwise to a stirred solution of 2,3-dihydro-1-hydroxyimino-1H-indene (100.8 g) in pyridine (600 ml) at 0°–5°. The mixture was stirred for 3 hours at 0°, then was poured into water and the title compound filtered. This was washed several times with water and air-dried.

Yield: 212.0 g; m.p. 147°–148°.

2-AMINO-2,3-DIHYDRO-1H-INDEN-1-ONE HYDROCHLORIDE

A solution of sodium ethoxide in ethanol (prepared from 8.7 g of sodium and 440 ml of ethanol) was added dropwise to a mixture of 2,3-dihydro-1-[(4-methylphenyl)sulfonyloximino]-1H-indene (116.6 g) in toluene (2200 ml) stirred at 0°. The reaction was kept at −10°–5° under nitrogen for 19 hours, and filtered through celite. The filtrate was washed with water, then extracted with 1N HCl. The acidic extracts were concentrated on a rotary evaporator, and the residue was triturated with acetone and filtered to give the title compound.

Yield: 34.5 g; m.p. 230° (dec.).

1,8-DIHYDRO(OR 3,8-DIHYDRO)INDENO[1,2-d]IMIDAZOLE-2-THIOL

A mixture of 2-amino-1,3-dihydro-1H-inden-1-one HCl (25.3 g), potassium thiocyanate (14.5 g), and acetic acid (100 ml) was heated at reflux for 20 minutes. After cooling, the solid product was filtered, washed with acetic acid and water, and air-dried to give the title compound.

Yield: 16.2 g; m.p. >250°.

1,8-DIHYDRO(OR 3,8-DIHYDRO)-2-(TRIFLUOROMETHYLTHIO)-INDENO[1,2-d]IMIDAZOLE

Liquid ammonia (1000 ml) was condensed in a flask (fitted with a dry-ice condenser) containing 1,8-dihydro(or 3,8-dihydro)indeno[1,2-d]imidazole-2-thiol (16.6 g). Tetrahydrofuran (275 ml) was added to obtain a homogenous solution. The mixture was stirred at −78° and treated with trifluoromethyl iodide (14.6 ml of liquid) added slowly as a gas. When the addition was complete, the mixture was warmed to reflux (−33°) and irradiated for 4 hours with a General Electric 275 watt sun lamp. The ammonia was then allowed to evaporate, and the remaining solvent removed on a rotary evaporator. The resulting solid was recrystallized from toluene.

Yield: 11.3 g; m.p. 205°-215° (dec.).

1,8-DIHYDRO(OR 3,8-DIHYDRO)-2-(1,1,2,2-TETRAFLUOROETHYLTHIO)INDENO-[1,2-d]IMIDAZOLE

To a stainless steel tube was added 1,8-dihydro(or 3,8-dihydro)indeno[1,2-d]imidazole-2-thiol (4.9 g), N,N-dimethylformamide (155 ml), and diisopropylamine (2.6 g). After purging the tube several times with dry nitrogen, tetrafluoroethylene (2.6 g) was introduced. The tube was agitated at 50° for 8 hours. The reaction mixture was poured into water and extracted with ethyl acetate. The organic phase was dried and concentrated on a rotary evaporator. The residue was recrystallized from toluene to provide the title product.

Yield: 3.7 g; m.p. 172°-176°.

Mixture of 1,8-DIHYDRO-1-(1-ETHOXYETHYL)-2-(TRIFLUOROMETHYLTHIO)INDENO[1,2-d]IMIDAZOLE and 3,8-DIHYDRO-3-(1-ETHOXYETHYL)-2-(TRIFLUOROMETHYLTHIO)INDENO[1,2-d]-IMIDAZOLE A mixture of 1,8-dihydro(or 3,8-dihydro)-2-(trifluoromethylthio)indeno[1,2-d]-imidazole (11.0 g), ethyl vinyl ether (20.8 ml), dichloroacetic acid (3.4 ml), and ethyl acetate (125 ml) was heated at reflux for 2 hours. After cooling, the mixture was diluted with ether, washed with saturated sodium bicarbonate solution, dried over magnesium sulfate, and concentrated on a rotary evaporator. The residue was dissolved in ether (100 ml) and stirred vigorously with a 20% aqueous solution of sodium hydroxide for 16 hours. The organic phase was washed with water, dried over magnesium sulfate, and evaporated to give the title mixture as a viscous brown syrup.

Yield: 14.1 g.

EXAMPLES 1 AND 2

1,8-DIHYDRO(OR 3,8-DIHYDRO)-2-(TRIFLUOROMETHYLTHIO)-8-(PHENYLMETHYLENE)INDENO[1,2-d]IMIDAZOLE, Z AND E ISOMERS

A solution of the mixture of 1,8-dihydro-1-(1-ethoxyethyl)-2-(trifluoromethylthio)indeno[1,2-d]imidazole and 3,8-dihydro-3-(1-ethoxyethyl)-2-(trifluoromethylthio)indeno[1,2-d]imidazole (2.0 g) (as isolated from the reaction described above) in ethanol (10 ml) was added to a solution of sodium ethoxide (from 0.02 g of sodium and 25 ml of ethanol). Benzaldehyde (0.8 ml) was added, and the mixture was heated at reflux for 2 hours. After cooling, 1N HCl (10 ml) was added, and the mixture was stirred at room temperature for 17 hours. The mixture was diluted with water and extracted with ethyl acetate, and the extracts were dried over magnesium sulfate and concentrated on a rotary evaporator. The crude product mixture was chromatographed on a silica gel column, using toluene-ethyl acetate (98:2) as the eluant. Two yellow products were obtained; the first to elute was recrystallized from tetrachloromethane to give the Z isomer of the title compound (Example 1).

Yield: 0.7 g; m.p. 154°-156°.

The second yellow product to elute was recrystallized from water-ethanol to provide the E isomer of the title compound (Example 2).

Yield: 0.6 g; m.p. 88°-95° (dec.).

EXAMPLE 3

1,8-DIHYDRO(OR 3,8-DIHYDRO)-2-(TRIFLUOROMETHYLSULFONYL)-8-(PHENYLMETHYLENE)INDENO[1,2-d]-IMIDAZOLE, Z ISOMER

A mixture of 1,8-dihydro(or 3,8-dihydro)-2-(trifluoromethylthio)-8-phenylmethylene-indeno[1,2-d]imidazole, Z isomer (1.8 g), 85% m-chloroperbenzoic acid (2.6 g), and ethyl acetate (50 ml) was stirred at room temperature for 112 hours, then washed with 5% sodium bisulfite and 10% sodium bicarbonate. The organic phase was dried over magnesium sulfate and concentrated on a rotary evaporator. The residue was chromatographed on a silica gel column with toluene-ethyl acetate (95:5) as the eluant. The product was titurated with hexane to provide the title compound.

Yield: 1.0 g; m.p. 208° (dec).

EXAMPLE 4

1,8-DIHYDRO(OR 3,8-DIHYDRO)-2-(TRIFLUOROMETHYLSULFONYL)-8-[(4-METHOXYPHENYL)METHYL]INDENO[1,2-d]-IMIDAZOLE

A mixture of 1,8-dihydro(or 3,8-dihydro)-2-(trifluoromethylsulfonyl)-8-[(4-methoxyphenyl)methylene]-indeno[1,2-d]imidazole, Z isomer (0.25 g), 10% palladium on charcoal (0.22 g), and glacial acetic acid (25 ml) was agitated at room temperature for 5 hours under an atmosphere of hydrogen at 45 psi. After filtration through celite, the solution was diluted with 200 ml water. The resulting solid was isolated by filtration, dried, and recrystallized from toluene to give the title compound.

Yield: 0.13 g; m.p. 206°–210°.

The compounds of Examples 1–4, as well as other 1,8-dihydro(or 3,8-dihydro)-2-(substituted thio)-8-(arylmethylene)indeno[1,2-d]imidazoles and their corresponding sulfoxides or sulfones (Examples 5–16) that were prepared by the procedures described in the above Examples are given in Tables 1 and 2.

TABLE 1

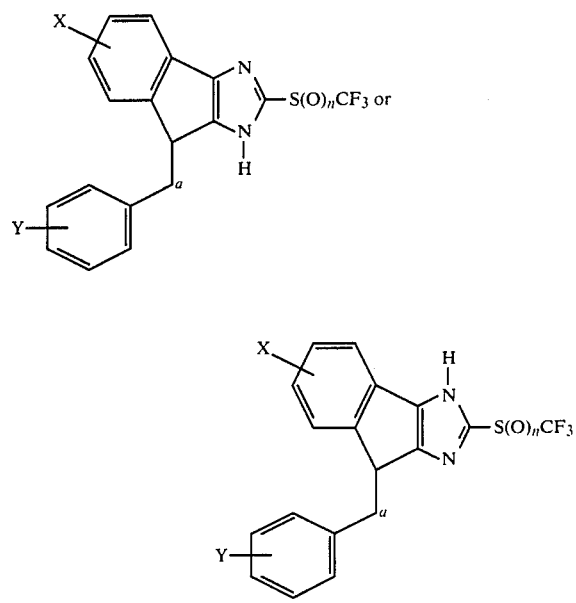

| Ex. | X,Y | n | Bond a* | m.p. | Yield (%) |
|---|---|---|---|---|---|
| 1 | H,H | 0 | Z olefin | 154–156° | 33 |
| 2 | H,H | 0 | E olefin | 88–95° (dec) | 29 |
| 3 | H,H | 2 | Z olefin | 208° (dec) | 50 |
| 4 | H,4'-OMe | 2 | Single | 206–210° (dec) | 52 |
| 5 | H,H | 2 | E olefin | 160–164° | 41 |
| 6 | H,4'-OMe | 0 | Z olefin | 169–172° | 20 |
| 7 | H,4'-OMe | 0 | E olefin | 180–190° | 32 |
| 8 | H,4'-OMe | 2 | Z olefin | 226–232° (dec) | 41 |
| 9 | H,4'-OMe | 2 | E olefin | 170–174° (dec) | 33 |
| 10 | H,4'-F | 0 | Z olefin | 165–167° | 24 |
| 11 | H,4'-F | 0 | E olefin | 170–175° | 29 |
| 12 | H,4'-F | 1 | E olefin | 190–192° (dec) | 73 |
| 13 | H,4'-F | 2 | Z olefin | 245° (dec) | 56 |
| 14 | H,4'-F | 2 | E olefin | 144° (dec) | 39 |

*The configuration about the double bond of the arylmethylene substituent conforms to standard nomenclature rules; the isomer with the imidazole ring and the arylmethylene ring in a cis relationship is the Z isomer; the isomer with the imidazole and the arylmethylene rings in a trans relationship is the E isomer.

TABLE 2

| EX. | R¹ | R² | m.p. | Yield (%) |
|---|---|---|---|---|
| 15 | CF₃ | CH(OEt)CH₃ | 145–146.8° | 25 |
| 16 | CF₂CF₂H | H | 65–85° | 38 |

Using the procedures described above, the following 1,8-dihydro(or 3,8-dihydro)-2-[(substituted)thio]-8-(arylmethylene)indeno[1,2-d]imidazoles, 1,8-dihydro(or 3,8-dihydro)-2-[(substituted)thio]-8-(arylmethyl)indeno-[1,2-d]imidazoles, and their corresponding sulfoxides and sulfones (Examples 17–30), can be prepared (Table 3).

TABLE 3

| Ex. | R¹ | R² | n | a* | X, Y |
|---|---|---|---|---|---|
| 17 | CF₃ | H | 2 | E olefin | 5-CH₃, H |
| 18 | CF₃ | COOCH₃ | 0 | E olefin | H, H |
| 19 | CF₃ | H | 2 | single bond | 6-F, 4'-F |
| 20 | CH₃ | CH₃ | 2 | E olefin | 5-CH₃, 4'-CH₃ |
| 21 | C₂H₅ | CH₂C₆H₅ | 0 | E olefin | 5-CH₃, 4'-OCH₃ |
| 22 | CF₂CF₂H | 2-THP | 0 | E olefin | 5-Cl, 3'-CH₃ |
| 23 | CF₃ | H | 2 | Z olefin | ** |
| 24 | CF₂CF₂H | COCH₃ | 0 | E olefin | 6-CH₃, 4'-OCH₃ |

TABLE 3-continued

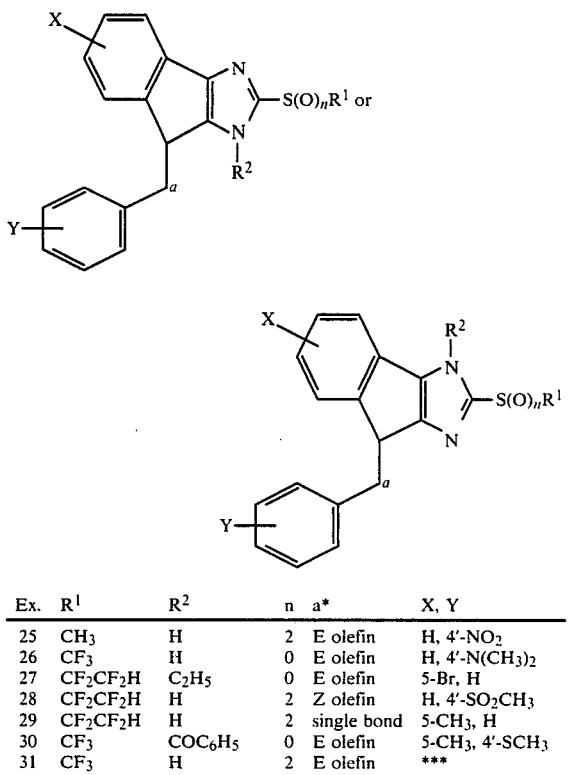

| Ex. | R$^1$ | R$^2$ | n | a* | X, Y |
|---|---|---|---|---|---|
| 25 | CH$_3$ | H | 2 | E olefin | H, 4'-NO$_2$ |
| 26 | CF$_3$ | H | 0 | E olefin | H, 4'-N(CH$_3$)$_2$ |
| 27 | CF$_2$CF$_2$H | C$_2$H$_5$ | 0 | E olefin | 5-Br, H |
| 28 | CF$_2$CF$_2$H | H | 2 | Z olefin | H, 4'-SO$_2$CH$_3$ |
| 29 | CF$_2$CF$_2$H | H | 2 | single bond | 5-CH$_3$, H |
| 30 | CF$_3$ | COC$_6$H$_5$ | 0 | E olefin | 5-CH$_3$, 4'-SCH$_3$ |
| 31 | CF$_3$ | H | 2 | E olefin | *** |

*The configuration about the double bond of the arylmethylene substituent conforms to standard nomenclature rules; the isomer with the imidazole ring and the arylmethylene ring in a cis relationship is the Z isomer; the isomer with the imidazole and arylmethylene rings in a trans relationship is the E isomer.
**Q = thienyl, X = H
***Q = 3 pyridyl, X = H

Dosage Forms

The antiinflammatory agents of this invention can be administered to treat inflammation by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference test in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol, solution, U.S.P., and 0.025 milliliters of vanillin.

Use

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, 32 (2), (1973) "Models Used for the Study and Therapy of Rheumatoid Arthritis"-Symposium of the American Society for Pharmacology and Experimental Therapeutics-states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Male Charles River Lewis rats (130-150 grams) are injected subcutaneously in the plantar area of the right hind paw with 0.1 ml of adjuvant (Difco heat-killed, lyophilized *Mycobacterium butyricum* suspended in mineral oil 5 mg/ml). Twenty non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound formulated in an appropriate vehicle or vehicle alone (10 ml/kg) by gavage on that day and on the 6 following days. The vehicle used is either PVA-Acacia (Polyvinyl Alcohol 1% Gum acacia, U.S.P. 5%, Methyl-parben 0.5%) or 0.25% Methocel (methycellulose: DOW Chemical type AI5C, viscosity 1500 CPS). One day after the last dose the paw volumes (uninjected, left hind paw) are measured using a Ugo Basile Volume Differential Meter Model 7101.

$$\frac{\frac{\text{Arthritic Control}}{\text{Mean Paw Volume (ml)}} - \frac{\text{Treatment Group}}{\text{Mean Paw Volume (ml)}}}{\frac{\text{Arthritic Control}}{\text{Mean Paw Volume (ml)}} - \frac{\text{Non-Arthritic Control}}{\text{Mean Paw Volume (ml)}}} \times 100 =$$

% Decrease from Control Mean Paw Volume

Dose-response regression lines of the percent decrease are plotted on semi-log paper by visual fit and the ED$_{50}$% decrease from control paw volume is determined by inspection. Data for the compounds in this invention are summarized in Table 4.

Compounds from this series were also compared to indomethacin, phenylbutazone, ibuprofen, and aspirin.

Phenylquinone Writhing Test

A standard procedure for detecting and comparing the analgesic activity of compounds in this series for which there is a good correlation with human efficacy is the standard phenylquinone writhing test modified from Siegmund, et al., *Proc. Soc. Exp. Biol. Med.*, 95, 729 (1957). A test compound suspended in 1% methylcellulose was given orally to fasted (17-21 hours) female white mice, 5-20 animals per double blind test. Aqueous (0.01% phenyl-p-benzoquinone)phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice (ED$_{50}$) was calculated by the moving average method of Thompson, W. R., *Bact. Rev.*, 11, 115-145 (1947). Data for some of the compounds is summarized in Table 4 together with data for some standard analgetic antiinflammatory drugs.

Prostaglandin Synthetase Inhibition Assay

Inhibition of bovine seminal vesicle prostaglandin synthetase (PGS) was measured by the method of White and Glassman [Prostaglandins, 7, 123-129 (1974)] as modified by Vigdahl and Tukey [*Biochem. Pharmacol.*, 26, 307-311 (1977)]. $^{14}$C-Arachidonic acid was used as a substrate at a final concentration of 0.02 mM. The resulting labelled prostaglandins were isolated on small columns of Bio-Sil® A silica gel. The reaction was buffered with 0.13M Tris.Cl (pH 8.5) and included 0.6 mM epinephrine, 2.1 mM reduced glutathione, and 0.09 mM EDTA, which favored PGE$_2$ as the primary product [C. Takeguchi, et al., *Biochem.*, 10, 2372-2376 (1971)]. Miles bovine seminal vesicle prostaglandin synthetase (20 μg), inhibitor, cofactor, and buffer were mixed and preincubated for two minutes at 37° C. The substrate was added to initiate the reaction which was run for 10 minutes. The reaction was stopped by freezing in a slurry of dry ice/ethanol. All reactions were run in duplicate. Inhibitors were bead-milled overnight and diluted in reaction buffer (0.2M Tris.Cl, pH 8.5). Inhibition was calculated by the following formula:

$$\% \text{ Inhibition} = 1 - \frac{(\text{DPM inhibited}) - (\text{DPM blank})}{(\text{DPM uninhibited}) - (\text{DPM blank})} \times 100\%$$

A semilog plot of percent inhibition versus final concentration of inhibitor was used to determine by inspection the concentration that inhibited the reaction by 50% (IC50). IC$_{50}$ values for some of the compounds of this invention as well as some standard prostaglandin synthetase inhibitors are summarized in Table 4.

TABLE 4

| Ex. | Adjuvant Arthritis ED$_{50}$ (mg/kg) | PQW ED$_{50}$ (mg/kg) | PGS IC$_{50}$ (μM) |
|---|---|---|---|
| 2 | (12% @ 9 mg/kg)[1,2] | 35 | <75 |
| 3 | (37% @ 9 mg/kg) | >81 | 0.93 |
| 4 | NT[3] | NT | 1.2 |
| 5 | 5.3 | 1.0 | 0.023 |
| 7 | (39% @ 9 mg/kg) | >108 | 0.58 |
| 8 | (5% @ 9 mg/kg)[2] | >36 | 0.31 |
| 9 | | 1.95 | 1.44 | 0.02 |
| 11 | (39% @ 9 mg/kg) | 21 | 2.7 |
| 12 | (48% @ 9 mg/kg) | 0.76 | 0.48 |
| 13 | 9.8 | 53.6 | 0.42 |
| Indomethacin | 0.25 | 0.35 | 3.2 |
| Phenylbutazone | 10 | 80 | 270 |
| Ibuprofen | 80 | 10 | 95 |

| Ex. | Adjuvant Arthritis ED$_{50}$ (mg/kg) | PQW ED$_{50}$ (mg/kg) | PGS IC$_{50}$ (μM) |
|---|---|---|---|
| Aspirin | 305 | 135 | 2200 |

[1] Numbers in parentheses indicate decrease in paw volume from controls at dose indicated.
[2] Although inactive at the dose tested, compound is believed to be active if tested at higher doses.
[3] NT = not tested.

What is claimed is:

1. A compound of the formula:

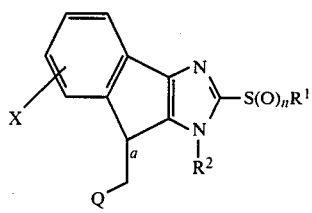

(Ia)

or

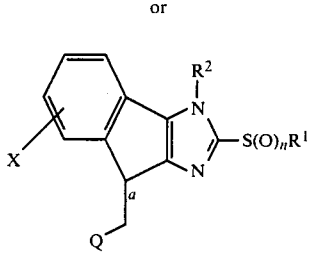

(Ib)

where
n is 0, 1 or 2;
R$^1$ is C$_1$–C$_2$ alkyl, CF$_3$ or CF$_2$CHF$_2$;
R$^2$ is H, C$_1$–C$_2$ alkyl, CH(R$^3$)OR$^4$, 2-tetrahydrofuranyl, 2-tetrahydropyranyl, COOR$^4$ or COR$^5$;
where
R$^3$ is H or CH$_3$;
R$^4$ is CH$_3$, C$_2$H$_5$ or

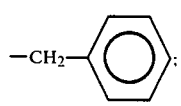

and
R$^5$ is CH$_3$ or C$_2$H$_5$; with the proviso that when R$^2$ is COOR$^4$ or COR$^5$, then n is 0;
a is a single bond or a double bond having either the E or Z configuration with the proviso that when the double bond is Z, then n is 1 or 2;
Q is pyridyl, thienyl or

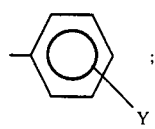

and
X and Y are independently H, F, Cl, Br, NO$_2$, OCH$_3$, OC$_2$H$_5$, N(C$_1$–C$_2$ alkyl)$_2$, CH$_3$, C$_2$H$_5$ or S(O)$_m$- C$_1$–C$_2$ alkyl where m is 0, 1 or 2; or
a pharmaceutically acceptable acid salt thereof when n is 0 or metal salt thereof when n is 2 and R$^2$ is H.

2. A compound of claim 1 wherein a is a double bond.
3. A compound of claim 1 wherein
n is 0 or 2;
R$^1$ is CF$_3$ or CF$_2$CHF$_2$;
R$^2$ is H;
a is a double bond;
Q is

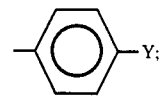

and
X and Y are independently H, F, Cl, OCH$_3$, CH$_3$ or S(O)$_m$CH$_3$ where m is 0 or 2.

4. A compound of claim 3 wherein R$^1$ is CF$_3$.
5. The compound of claim 1 which is 1,8-dihydro(or 3,8-dihydro)-2-(trifluoromethylsulfonyl)-8-(phenylmethylene)indeno[1,2-d]imidazole, E isomer.
6. The compound of claim 1 which is 1,8-dihydro(or 3,8-dihydro)-2-(trifluoromethylsulfonyl)-8-[(4-methoxyphenyl)methylene]indeno[1,2-d]imidazole, E isomer.
7. The compound of claim 1 which is 1,8-dihydro(or 3,8-dihydro)-2-(trifluoromethylsulfinyl)-8-[(4-fluorophenyl)methylene]indeno[1,2-d]imidazole, E isomer.
8. A pharmaceutical composition for treating inflammation or primary dysmenorrhea comprising an effective antiinflammatory or anti-primary dysmenorrheal amount of at least one compound of claim 1 and a pharmaceutically acceptable carrier.
9. A pharmaceutical composition for treating inflammation, primary dysmenorrhea or pain comprising an effective antiinflammatory, anti-primary dysmenorrheal, or analgesic amount of at least one compound of claim 1 wherein n=1 or 2 and a is a double bond of the E configuration and a pharmaceutically acceptable carrier.
10. The composition of claim 9 wherein the compound is selected from the group consisting of 1,8-dihydro(or 3,8-dihydro)-2-(trifluoromethylsulfonyl)-8-(phenylmethylene)indeno[1,2-d]imidazole, E isomer, 1,8-dihydro(or 3,8-dihydro)-2-(trifluoromethylsulfonyl)-8-[(4-methoxyphenyl)methylene]indeno[1,2-d]imidazole, E isomer and 1,8-dihydro(or 3,8-dihydro)-2-(trifluoromethylsulfinyl)-8-[(4-fluorophenyl)methylene]indeno[1,2-d]imidazole, E isomer.
11. A method for treating inflammation or primary dysmenorrhea in a mammal which comprises administering to the mammal an effective amount of at least one compound of claim 1.
12. A method for treating inflammation or primary dysmenorrhea in a mammal which comprises administering to the mammal an effective amount of at least one compound of claim 2.
13. A method for treating inflammation or primary dysmenorrhea a mammal which comprises administering to the mammal an effective amount of at least one compound of claim 3.
14. A method for treating inflammation or primary dysmenorrhea in a mammal which comprises adminto the mammal an effective amount of at least one compound of claim 4.
15. A method for treating of pain, inflammation or primary dysmenorrhea in a mammal comprising administering an effective amount of the compound of claim 5.

16. A method for treatment of pain, inflammation or primary dysmenorrhea in a mammal comprising administering an effective amount of the compound of claim 6.

17. A method for treatment of pain, inflammation or primary dysmenorrhea in a mammal comprising administering an effective amount of the compound of claim 7.

18. A method for treatment of pain, inflammation or primary dysmenorrhea in a mammal comprising administering an effecive amount of a compound of claim 1 wherein n=1 or 2 and a is a double bond having the E configuration.

19. A compound of the formula:

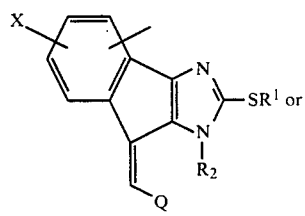

-continued

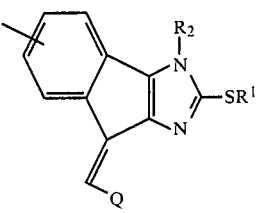

where
$R^1$ is $C_1$–$C_2$ alkyl, $CF_3$ or $CF_2CHF_2$;
$R^2$ is H, $C_1$–$C_2$ alkyl, $CH(R^3)OR^4$, 2-tetrahydrofuranyl, 2-tetrahydropyranyl, $COOR^4$ or $COR^5$;
where
$R^3$ is H or $CH_3$;
$R^4$ is $CH_3$, $C_2H_5$ or

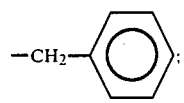

and
$R^5$ is $CH_3$ or $C_2H_5$;
Q is pyridyl, thienyl or

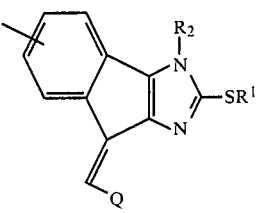

and
X and Y are independently H, F, Cl, Br, $NO_2$, $OCH_3$, $OC_2H_5$, $N(C_1$–$C_2$ alkyl$)_2$, $CH_3$, $C_2H_5$ or $S(O)_m$-$C_1$–$C_2$alkyl where m is 0, 1 or 2.

* * * * *